(12) United States Patent
Chappa

(10) Patent No.: US 11,318,204 B2
(45) Date of Patent: May 3, 2022

(54) COMPOSITION FOR INTRAVASCULAR DELIVERY OF THERAPEUTIC COMPOSITION

(71) Applicant: Surmodics, Inc., Eden Prairie, MN (US)

(72) Inventor: Ralph A. Chappa, Ham Lake, MN (US)

(73) Assignee: Surmodics, Inc., Eden Prairie, MN (US)

( * ) Notice: Subject to any disclaimer, the term of this patent is extended or adjusted under 35 U.S.C. 154(b) by 0 days.

(21) Appl. No.: 15/373,174

(22) Filed: Dec. 8, 2016

(65) Prior Publication Data

US 2017/0095559 A1    Apr. 6, 2017

Related U.S. Application Data

(63) Continuation of application No. 14/613,532, filed on Feb. 4, 2015, now abandoned, which is a continuation of application No. 13/339,908, filed on Dec. 29, 2011, now abandoned.

(60) Provisional application No. 61/428,397, filed on Dec. 30, 2010.

(51) Int. Cl.
| | |
|---|---|
| *A61K 47/22* | (2006.01) |
| *A61K 9/00* | (2006.01) |
| *A61K 31/337* | (2006.01) |
| *A61M 25/00* | (2006.01) |
| *A61K 31/436* | (2006.01) |
| *A61M 25/10* | (2013.01) |
| *A61L 29/16* | (2006.01) |

(52) U.S. Cl.
CPC ............ *A61K 47/22* (2013.01); *A61K 9/0019* (2013.01); *A61K 31/337* (2013.01); *A61K 31/436* (2013.01); *A61L 29/16* (2013.01); *A61M 25/0026* (2013.01); *A61M 25/0045* (2013.01); *A61M 25/1011* (2013.01); *A61L 2300/416* (2013.01); *A61M 25/0009* (2013.01); *A61M 25/1029* (2013.01); *A61M 2025/1004* (2013.01); *A61M 2025/105* (2013.01); *A61M 2025/1013* (2013.01); *A61M 2025/1088* (2013.01)

(58) Field of Classification Search
None
See application file for complete search history.

(56) References Cited

U.S. PATENT DOCUMENTS

| | | | |
|---|---|---|---|
| 4,195,637 A | 4/1980 | Gruntig et al. | |
| 4,490,421 A | 12/1984 | Levy | |
| 5,041,089 A | 8/1991 | Mueller et al. | |
| 5,087,246 A | 2/1992 | Smith | |
| 5,213,576 A * | 5/1993 | Abiuso | A61M 25/104 604/103.01 |
| 5,318,587 A | 6/1994 | Davey | |
| 5,382,234 A | 1/1995 | Cornelius et al. | |
| 5,530,006 A | 6/1996 | Waranis et al. | |
| 5,556,383 A | 9/1996 | Wang et al. | |
| 5,571,089 A | 11/1996 | Crocker | |
| 5,776,101 A | 7/1998 | Goy | |
| 5,807,331 A | 9/1998 | den Heijer et al. | |
| 5,882,336 A | 3/1999 | Janacek | |
| 6,004,973 A | 12/1999 | Guitard et al. | |
| 6,007,833 A | 12/1999 | Chudzik et al. | |
| 6,017,948 A | 1/2000 | Rubinfeld et al. | |
| 6,040,330 A | 3/2000 | Hausheer et al. | |
| 6,168,748 B1 | 1/2001 | Wang et al. | |
| 6,210,364 B1 | 4/2001 | Anderson et al. | |
| 6,294,192 B1 | 9/2001 | Patel et al. | |
| 6,328,710 B1 | 12/2001 | Wang et al. | |
| 6,394,995 B1 | 5/2002 | Solar et al. | |
| 6,482,348 B1 | 11/2002 | Wang et al. | |
| 6,517,515 B1 | 2/2003 | Eidenschink | |
| 6,623,504 B2 | 9/2003 | Vrba et al. | |
| 6,703,040 B2 | 3/2004 | Katsarava et al. | |
| 6,896,842 B1 | 5/2005 | Hamilton et al. | |
| 7,163,523 B2 | 1/2007 | Devens, Jr. et al. | |
| RE40,359 E | 6/2008 | Katsarava et al. | |
| 2005/0064010 A1 | 3/2005 | Cooper et al. | |
| 2007/0218102 A1 | 9/2007 | Chudzik et al. | |
| 2007/0224247 A1 | 9/2007 | Chudzik et al. | |
| 2007/0260054 A1 | 11/2007 | Chudzlk | |
| 2007/0280992 A1 | 12/2007 | Margaron et al. | |
| 2008/0146651 A1 | 6/2008 | Jee et al. | |

(Continued)

FOREIGN PATENT DOCUMENTS

| | | |
|---|---|---|
| EP | 650730 A1 | 5/1995 |
| WO | WO 2005/068533 A1 | 7/2005 |
| WO | WO 2007/020085 | 2/2007 |

(Continued)

OTHER PUBLICATIONS

Wong "Outpatient Administration of Paclitaxel", cjhp vol. 6. Jul. 1994.*

(Continued)

*Primary Examiner* — Isis A Ghali

(74) *Attorney, Agent, or Firm* — Kagan Binder, PLLC

(57) ABSTRACT

The present invention relates to a pharmaceutical composition for intravascular delivery of a therapeutic agent, such as paclitaxel, rapamycin, or an analog thereof. The composition includes the therapeutic agent and a biocompatible solvent, such as glycofurol. The composition can aid tissue penetration by the therapeutic agent. A catheter assembly that protects the pharmaceutical composition from the surroundings can be used for its intravascular delivery.

10 Claims, No Drawings

(56) References Cited

U.S. PATENT DOCUMENTS

2009/0105686 A1* 4/2009 Snow ................ A61F 2/958
604/509

FOREIGN PATENT DOCUMENTS

| WO | WO 2008100576 A2 | 8/2008 | | |
|---|---|---|---|---|
| WO | WO-2009036135 A1 * | 3/2009 | ........ | A61M 25/1027 |

OTHER PUBLICATIONS

Shamseddine et al., "Comparative Pharmacokinetics and Metabolic Pathway of Gemcitabine During Intravenous and Intra-arterial Delivery in Unresectable Pancreatic Cancer Patient", Clin Pharmacokint 2005; 44 (9): 957-967. (Year: 2005).*

Ali et al., Kolliphor HS 15—An Enabler for Parenteral and Oral Formulations, American Pharmaceutical Review, Feb. 25, 2019, 18 pages.

Alani et al., The Effect of Novel Surfactants and Solutol HS15 on Paclitaxel Aqueous Solubility and Permeability Across the Caco-2 Monolayer, Journal of Pharmaceutical Sciences, vol. 99, No. 8, Aug. 2010, pp. 3474-3485.

Dake, M.D., et al. (2011) "Paclitaxel-Eluting Stents Show Superiority to Balloon Angioplasty and Bare Metal Stents in Femoropopliteal Disease—Twelve-Month Zilver PTX Randomized Study Results", Circ. Cardiovasc. Interv., 4:495-504.

Ellis, S.G., et al. (2009) "Long-Term Safety and Efficacy With Paclitaxel-Eluting Stents", JACC: Cardiovascular Interventions, 2(12):1248-1259.

Weisz, G., et al. (2009) "Five-Year Follow-Up After Sirolimus-Eluting Stent Implantation", Journal of the American College of Cardiology, 53(17):1488-1497.

Dake, M.D., et al. (2011) "Nitinol Stents With Polymer-Free Paclitaxel Coating for Lesions in theSuperficial Femoral and Popliteal Arteries Above the Knee: Twelve-Month Safety and Effectiveness Results From the Zilver PTX Single-Arm Clinical Study", J. Endovasc. Ther. 18(5):613-623 (abstract only).

* cited by examiner

COMPOSITION FOR INTRAVASCULAR DELIVERY OF THERAPEUTIC COMPOSITION

CROSS-REFERENCE TO RELATED APPLICATION

This application is a continuation of U.S. application Ser. No. 14/613,532, filed Feb. 4, 2015, which is a continuation of U.S. application Ser. No. 13/339,908 filed Dec. 29, 2011, now abandoned, which claims the benefit of U.S. Provisional Application No. 61/428,397 filed Dec. 30, 2010, the entire contents of which are incorporated herein by reference for all purposes.

FIELD OF THE INVENTION

The present invention relates to a pharmaceutical composition for intravascular delivery of a therapeutic agent, such as paclitaxel, rapamycin, or an analog thereof. The composition includes the therapeutic agent and a biocompatible solvent, such as glycofurol. The composition can aid tissue penetration by the therapeutic agent. A catheter assembly that protects the pharmaceutical composition from the surroundings can be used for its intravascular delivery.

BACKGROUND OF THE INVENTION

The release of drugs from an implanted medical device has been shown to be beneficial for the function of devices and the treatment of various medical conditions. For example, delivery of a drug from the device surface can prevent cellular responses initiated by the presence of the implantable device. Also, drug released from the device can prevent conditions that would otherwise shorten the functional life of the device following implantation. Drug released from the device may also be directed at treating a diseased area of the body.

Some implantable devices simply have a drug applied to the device surface. Such preparations are generally undesirable because the drug can be easily removed from the surface during insertion.

Implantable medical devices having thin polymeric coatings containing therapeutic compounds protect and control the release of drug from the device surface. Such devices have been shown to be particularly valuable for the treatment of diseases of the cardiovascular system. However, these polymeric coatings may not be ideal for applications involving the transient insertion of a medical device to a target tissue in the body.

SUMMARY OF THE INVENTION

The present invention relates to a pharmaceutical composition for intravascular delivery of a therapeutic agent, such as paclitaxel, rapamycin, or an analog thereof. The composition includes the therapeutic agent and a biocompatible solvent, such as glycofurol. The composition can aid tissue penetration by the therapeutic agent. A catheter assembly that protects the pharmaceutical composition from the surroundings can be used for its intravascular delivery.

The present pharmaceutical composition can include about 1 to about 50 wt-% therapeutic agent and about 50 to about 99 wt-% biocompatible solvent. The present pharmaceutical composition can include about 10 to about 40 wt-% biodegradable polymer and about 60 to about 90 wt-% biocompatible solvent. The present pharmaceutical composition can include about 2 to about 30 wt-% paclitaxel and about 70 to about 98 wt-% glycofurol.

The present composition can be a component of a drug delivery device, such as an intravascular catheter, that includes a reservoir. The reservoir can contain the present pharmaceutical composition. The reservoir can be a lumen (i.e., a third lumen) with the catheter shaft. The reservoir can be a cavity defined by two balloons, one inside the other, of a balloon catheter.

DETAILED DESCRIPTION OF THE INVENTION

The present invention relates to a pharmaceutical composition for intravascular delivery of a therapeutic agent or biodegradable polymer. The present pharmaceutical composition can include a biocompatible solvent (e.g., glycofurol) and a therapeutic agent (e.g., paclitaxel), a biodegradable polymer, or a mixture thereof. In an embodiment, the present pharmaceutical composition includes a biocompatible solvent (e.g., glycofurol) and a therapeutic agent (e.g., paclitaxel). In an embodiment, the present pharmaceutical composition includes a biocompatible solvent (e.g., glycofurol) and a biodegradable polymer. In an embodiment, the present pharmaceutical composition includes a biocompatible solvent (e.g., glycofurol) and a therapeutic agent (e.g., paclitaxel) and a biodegradable polymer. In an embodiment, delivery of the composition to a site in the vasculature results in tissue penetration by the therapeutic agent. In an embodiment, delivery of the composition to a site in the vasculature results in deposit of a solid or semisolid form of the therapeutic agent at the site. In an embodiment, delivery of the composition to a site in the vasculature results in solidification of the biodegradable polymer at the site.

The present pharmaceutical composition can include, for example, about 1 to about 50 wt-% therapeutic agent and about 50 to about 99 wt-% biocompatible solvent. In an embodiment, the present pharmaceutical composition includes about 5 to about 40 wt-% therapeutic agent and about 60 to about 95 wt-% biocompatible solvent. In an embodiment, the present pharmaceutical composition includes about 10 to about 30 wt-% therapeutic agent and about 70 to about 90 wt-% biocompatible solvent. In an embodiment, the present pharmaceutical composition includes about 5 to about 15 wt-% therapeutic agent and about 85 to about 95 wt-% biocompatible solvent. In an embodiment, the present pharmaceutical composition includes about 10 to about 20 wt-% therapeutic agent and about 80 to about 90 wt-% biocompatible solvent. In an embodiment, the present pharmaceutical composition includes about 20 to about 30 wt-% therapeutic agent and about 70 to about 80 wt-% biocompatible solvent.

In an embodiment, the present pharmaceutical composition includes about 2 to about 20 wt-% therapeutic agent and about 80 to about 98 wt-% biocompatible solvent. In an embodiment, the present pharmaceutical composition includes about 5 to about 10 wt-% therapeutic agent and about 90 to about 95 wt-% biocompatible solvent.

In an embodiment, the biocompatible solvent includes glycofurol, ethyl heptanoate, ethyl octanoate, benzyl benzoate, glycerol tributyrate, dimethyl isosorbide, glycerol triacetate (triacetin), glycerol tributyrate, dimethyl sulfoxide (DMSO), N-methyl-2-pyrrolidone (NMP), methanol, ethanol, isopropyl alcohol, dimethylformamide (DMF), dimethylacetamide (DMAC), or a mixture thereof. In an embodiment, the biocompatible solvent can include an aliphatic ester. In an embodiment, the biocompatible solvent can include an alkyl ester, an aryl ester, a glycerol ester (e.g., diester or triester), a benzyl alcohol, a propylene glycol, or a mixture thereof. The biocompatible solvent can be: one in which the therapeutic composition is soluble; water miscible; not volatile; or a combination thereof.

In an embodiment, the biocompatible solvent includes glycofurol. In an embodiment, the biocompatible solvent is glycofurol. Glycofurol has CAS no. 9004-76-6.

In an embodiment, the therapeutic agent is paclitaxel. In an embodiment, the therapeutic agent is rapamycin (sirolimus) or a rapamycin analog (a rapalog). Suitable rapalogs include temsirolimus (CCI-779; Wyeth, Madison, N.J., US), everolimus (RAD001; Novartis, Basel, Switzerland), ridaforolimus (AP23573, formerly known as deforolimus; Merck & Co., Whitehouse Station, N.J., US), zotarolimus (ABT-578), and umirolimus (also called biolimus or biolimus A9).

The present composition can be dispensed at the desired site in the vasculature by any of a variety of delivery devices. For example, the present composition can be delivered by a catheter assembly that protects the pharmaceutical composition from the surroundings. In an embodiment, the present composition is within a lumen (e.g., a third lumen) within the catheter assembly. In an embodiment, the present composition is contained in a reservoir or cavity between two balloons of a balloon catheter. In an embodiment, the present composition is in a reservoir or cavity beneath (i.e., inside of) a balloon of a balloon catheter In an embodiment, the present composition can be delivered from a catheter assembly such as that described in U.S. patent application Ser. No. 61/428,353, filed Dec. 30, 2010, the disclosure of which is incorporated herein by reference. Such a catheter assembly can include an inner expandable and collapsible structure and an outer expandable and collapsible structure. The inner and outer expandable and collapsible structures can be configured to expand between a contracted state and a dilated state. The inner and outer expandable and collapsible structures define a cavity therebetween, which is configured to contain the present therapeutic composition. The outer expandable and collapsible structure defines openings. The openings being configured to be closed when the assembly is in the contracted state. The openings are configured to be open when the assembly is in the dilated state. When open, the openings provide fluid communication from the cavity to surroundings of the assembly.

Such a catheter assembly can protect the present therapeutic composition from its surroundings by retaining it in a reservoir between an inner and outer balloon. The therapeutic composition can be released from the assembly through openings in the outer balloon. When the assembly is in its contracted state, the openings are closed, and the assembly retains the therapeutic composition. Expanding the inner balloon (e.g., with fluid) urges the assembly to its dilated state, in which the openings are open, and the present therapeutic composition can leave the assembly. A lumen in fluid communication with the reservoir can increase the capacity of the assembly for the present therapeutic composition.

In another aspect, the present invention includes a method of delivering the present therapeutic composition to a site in a body. The method can employ the catheter assembly described above. This method includes placing the catheter assembly at the site and actuating the catheter assembly from the contracted state to the dilated state to release the present therapeutic composition.

Paclitaxel and Glycofurol

The present invention relates to a pharmaceutical composition for intravascular delivery of paclitaxel that can include paclitaxel and glycofurol. In an embodiment, the composition provides tissue penetration by paclitaxel. For example, when an embodiment of the composition is applied to an interior surface of a blood vessel ex vivo, the paclitaxel can be transported through the blood vessel and appear as a solid on the exterior of the blood vessel.

The present pharmaceutical composition can include, for example, about 1 to about 50 wt-% paclitaxel and about 50 to about 99 wt-% glycofurol. In an embodiment, the present pharmaceutical composition includes about 5 to about 40 wt-% paclitaxel and about 60 to about 95 wt-% glycofurol. In an embodiment, the present pharmaceutical composition includes about 2 to about 20 wt-% paclitaxel and about 80 to about 98 wt-% glycofurol. In an embodiment, the present pharmaceutical composition includes about 5 to about 10 wt-% paclitaxel and about 90 to about 95 wt-% glycofurol.

In an embodiment, the present pharmaceutical composition includes about 10 to about 30 wt-% paclitaxel and about 70 to about 90 wt-% glycofurol. In an embodiment, the present pharmaceutical composition includes about 5 to about 15 wt-% paclitaxel and about 85 to about 95 wt-% glycofurol. In an embodiment, the present pharmaceutical composition includes about 10 to about 20 wt-% paclitaxel and about 80 to about 90 wt-% glycofurol. In an embodiment, the present pharmaceutical composition includes about 20 to about 30 wt-% paclitaxel and about 70 to about 80 wt-% glycofurol.

In an embodiment, the present pharmaceutical composition includes about 10 wt-% paclitaxel and about 90 wt-% glycofurol. In an embodiment, the present pharmaceutical composition includes about 30 wt-% paclitaxel and about 70 wt-% glycofurol.

Biodegradable Polymer

The biodegradable polymer can include one or more (e.g., 1, 2, 3 or 4) specific biodegradable polymers, for use in forming an implant in vivo. Suitable polymers will be biodegradable and will be sufficiently soluble in the biocompatible solvent. In an embodiment, the biodegradable polymer has a solubility of at least about 50 g/L in the biocompatible solvent at 25° C. and 1 atm.

Suitable polymers include, e.g., polylactides, polyglycolides, polycaprolactones, polyanhydrides, polyamines, polyurethanes, polyesteramides, polyorthoesters, polydioxanones, polyacetals, polyketals, polycarbonates, polyorthocarbonates, polyphosphazenes, succinates, poly(malic acid), poly(amino acids), polyvinylpyrrolidone, polyethylene glycol, polyhydroxycellulose, polysaccharides, chitin, chitosan, and copolymers, block copolymers, multi-block co-polymers, multi-block co-polymers with polyethylene glycol (PEG), polyols, terpolymers and mixtures thereof.

In an embodiment, the biodegradable polymer is a thermoplastic polymer.

In an embodiment, the biodegradable polymer has a viscosity of at least about 100 cP at 37° C. In other embodiments, the biodegradable polymer has a viscosity of about 1,000 cP to about 30,000 cp at 37° C., about 5,000 cP to about 25,000 cp at 37° C., or about 10,000 cP to about 20,000 cp at 37° C.

In an embodiment, the biodegradable polymer is hydrophobic.

In an embodiment, the biodegradable polymer includes a block copolymer. In an embodiment, the biodegradable polymer is a polyethylene glycol (PEG) containing tri-block co-polymer.

In an embodiment the polymer contains functional side groups.

In an embodiment, the biodegradable polymer can include a poly(ether ester) multi-block copolymer. In an embodiment, the biodegradable polymer can include a polyglycerol fatty acid ester. In an embodiment, the biodegradable polymer can include a PEG-PBT polymer. In an embodiment, the biodegradable polymer can include a polyester amide. In an embodiment, the biodegradable polymer can include a poly(ester-amide) polymer (PEA).

The present pharmaceutical composition can include, for example, about 1 to about 50 wt-% biodegradable polymer and about 50 to about 99 wt-% biocompatible solvent. In an embodiment, the present pharmaceutical composition includes about 5 to about 40 wt-% biodegradable polymer and about 60 to about 95 wt-% biocompatible solvent. In an embodiment, the present pharmaceutical composition includes about 10 to about 30 wt-% biodegradable polymer and about 70 to about 90 wt-% biocompatible solvent. In an embodiment, the present pharmaceutical composition includes about 5 to about 15 wt-% biodegradable polymer and about 85 to about 95 wt-% biocompatible solvent. In an embodiment, the present pharmaceutical composition includes about 10 to about 20 wt-% biodegradable polymer and about 80 to about 90 wt-% biocompatible solvent. In an embodiment, the present pharmaceutical composition includes about 20 to about 30 wt-% biodegradable polymer and about 70 to about 80 wt-% biocompatible solvent. In an embodiment, the present pharmaceutical composition includes about 2 to about 20 wt-% biodegradable polymer and about 80 to about 98 wt-% biocompatible solvent. In an embodiment, the present pharmaceutical composition includes about 5 to about 10 wt-% biodegradable polymer and about 90 to about 95 wt-% biocompatible solvent.

Poly(Ether Ester) Multi-Block Copolymers

One suitable class of biodegradable polymers useful in the present invention includes the poly(ether ester) multi-block copolymers. Such multi-block copolymers are composed of various pre-polymer building blocks of different combinations of DL-lactide, glycolide, ε-caprolactone and polyethylene glycol. By varying the molecular composition, molecular weight (Mw 1200-6000) and ratio of the pre-polymer blocks, different functionalities can be introduced into the final polymer, which enables the creation of polymers with various physio-chemical properties. Both hydrophobic as well as hydrophilic/swellable polymers and slowly degrading as well as rapidly degrading polymers can be designed.

Suitable poly(ether ester) multi-block copolymers can include a polymer as shown below (formula III):

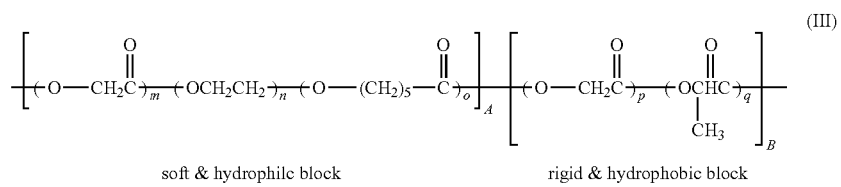

soft & hydrophilc block      rigid & hydrophobic block wherein,
m and p are each independently glycolide;
n is polyethylene glycol, Mw 300-1000;
o is ε-caprolactone; and
q is DL-lactide.

Additional features and descriptions of such poly(ether ester) multi-block copolymers are provided, for example, in Published PCT Patent Application No. WO 2005/068533 and references cited therein. The multi-block copolymers can specifically include two hydrolysable segments having a different composition, linked by a multifunctional, specifically an aliphatic chain-extender, and which are specifically essentially completely amorphous under physiological conditions (moist environment, body temperature, which is approximately 37° C. for humans).

The resulting multi-block copolymers can specifically have a structure according to any of the formulae (1)-(3):

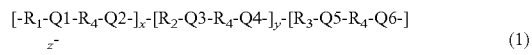

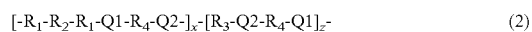

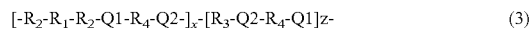

in which:

$R_1$ and $R_2$ can be amorphous polyester, amorphous poly ether ester or amorphous polycarbonate; or an amorphous pre-polymer that is obtained from combined ester, ether and/or carbonate groups. $R_1$ and $R_2$ can contain polyether groups, which can result from the use of these compounds as a polymerization initiator, the polyether being amorphous or crystalline at room temperature. However, the polyether thus introduced can become amorphous at physiological conditions. $R_1$ and $R_2$ are derived from amorphous pre-polymers or blocks A and B, respectively, and $R_1$ and $R_2$ are not the same. $R_1$ and $R_2$ can contain a polyether group at the same time. In a specific embodiment, only one of them will contain a polyether group;

z is zero or a positive integer;

$R_3$ is a polyether, such as poly(ethylene glycol), and may be present ($z\neq 0$) or not ($z=0$). $R_3$ will become amorphous under physiological conditions;

$R_4$ is an aliphatic $C_2$-$C_8$ alkylene group, optionally substituted by a $C_1$-$C_{10}$ alkylene, the aliphatic group being linear or cyclic, wherein $R_4$ can specifically be a butylene, —$(CH_2)_4$— group, and the $C_1$-$C_{10}$ alkylene side group can contain protected S, N, P or O moieties;

x and y are both positive integers, which can both specifically be at least 1, whereas the sum of x and y (x+y) can specifically be at most 1000, more specifically at most 500, or at most 100. Q1-Q6 are linking units obtained by the reaction of the pre-polymers with the multifunctional chain-extender. Q1-Q6 are independently amine, urethane, amide, carbonate, ester or anhydride.

PEG-PBT Polymers

One suitable class of biodegradable polymers useful in the present invention include the poly(ether ester) multiblock copolymers based on poly(ethylene glycol) (PEG) and poly(butylene terephthalate) (PBT), that can be described by the following general formula IV:

$$[-(OCH_2CH_2)_n-O-C(O)-C_6H_4-C(O)-]_x[-O-(CH_2)_4-O-C(O)-C_6H_4-C(O)-]_y, \quad (IV)$$

wherein,

—$C_6H_4$— designates the divalent aromatic ring residue from each esterified molecule of terephthalic acid, n represents the number of ethylene oxide units in each hydrophilic PEG block, x represents the number of hydrophilic blocks in the copolymer, and y represents the number of hydrophobic blocks in the copolymer.

In specific embodiments, n can be selected such that the molecular weight of the PEG block is between about 300 and about 4000. In specific embodiments, x and y can each be independently selected so that the multiblock copolymer contains from about 55% up to about 80% PEG by weight.

The block copolymer can be engineered to provide a wide array of physical characteristics (e.g., hydrophilicity, adherence, strength, malleability, degradability, durability, flexibility) and bioactive agent release characteristics (e.g., through controlled polymer degradation and swelling) by varying the values of n, x and y in the copolymer structure.

Polyester Amides

One suitable class of biodegradable polymers useful in the present invention includes the polyesteramide polymers having a subunit of the formula (V):

$$-[-O-(CH_2)_x-O-C(O)-CHR-NH-C(O)-(CH_2)_y-C(O)-NH-CHR-C(O)-]- \quad (V)$$

wherein, x is $C_2$-$C_{12}$, y is $C_2$-$C_{12}$, and

R is —$CH(CH_3)_2$, —$CH_2CH(CH_3)_2$, —$CH(CH_3)CH_2CH_3$, —$CH_2(CH_2)_2CH_3$, —$CH_2C_6H_5$, —$CH_2(CH_2)_2SCH_3$ or part of an amino acid.

In specific embodiments, the $C_2$-$C_{12}$ can be ($C_2$-$C_{12}$) alkyl. In other specific embodiments, the $C_2$-$C_{12}$ can be ($C_2$-$C_{12}$)alkyl, optionally substituted.

Such polymers are described, for example, in U.S. Pat. No. 6,703,040. Polymers of this nature can be described with a nomenclature of x-aa-y, wherein "x" represents an alkyl diol with x carbon atoms, "aa" represents an amino acid such as leucine or phenylalanine, and y represents an alkyldicarboxylic acid with y carbon atoms, and wherein the polymer is a polymerization of the diol, the dicarboxylic acid, and the amino acid. An exemplary polymer of this type is 4-Leu-4.

Poly(Ester-Amide) Polymer (PEA)

One suitable class of biodegradable polymers useful in the present invention includes the poly(ester-amide) polymers. Such polymers can be prepared by polymerization of a diol, a dicarboxylic acid and an alpha-amino acid through ester and amide links in the form $(DACA)_n$. An example of a $(DACA)_n$ polymer is shown below in formula VI. Suitable amino acids include any natural or synthetic alpha-amino acid, specifically neutral amino acids.

Diols can be any aliphatic diol, including alkylene diols like HO—$(CH_2)_k$—OH (i.e. non-branched), branched diols (e.g., propylene glycol), cyclic diols (e.g. dianhydrohexitols and cyclohexanediol), or oligomeric diols based on ethylene glycol (e.g., diethylene glycol, triethylene glycol, tetraethylene glycol, or poly(ethylene glycol)s). Aromatic diols (e.g. bis-phenols) are less useful for these purposes since they are more toxic, and polymers based on them have rigid chains that are less likely to biodegrade.

Dicarboxylic acids can be any aliphatic dicarboxylic acid, such as α-omega-dicarboxylic acids (i.e., non-branched), branched dicarboxylic acids, cyclic dicarboxylic acids (e.g. cyclohexanedicarboxylic acid). Aromatic diacids (like phthalic acids, etc.) are less useful for these purposes since they are more toxic, and polymers based on them have rigid chain structure, exhibit poorer film-forming properties and have much lower tendency to biodegrade.

Specific PEA polymers have the formula VI:

$$\left[ -O-(CH_2)_k-O-\overset{O}{\underset{\|}{C}}-\overset{H}{\underset{R}{C}}-\overset{H}{N}-\overset{O}{\underset{\|}{C}}-(CH_2)_m-\overset{O}{\underset{\|}{C}}-\overset{H}{N}-\overset{H}{\underset{R}{C}}-\overset{O}{\underset{\|}{C}}- \right]_n \quad (VI)$$

wherein, k is 2-12 (e.g., 2, 3, 4, or 6);

m is 2-12 (e.g., 4 or 8); and

R is —$CH(CH_3)_2$, —$CH_2CH(CH_3)_2$, —$CH(CH_3)CH_2CH_3$, —$CH_2(CH_2)_2CH_3$, —$CH_2(C_6H_5)$, or —$CH_2(CH_2)SCH_3$.

In specific embodiments, A is L-phenylalanine (Phe-PEA) and A is L-leucine (Leu-PEA). In specific embodiments, the ratio of Phe-PEA to Leu-PEA is from 10:1 to 1:1. In other specific embodiments, the ratio of Phe-PEA to Leu-PEA is from 5:1 to 2.5:1.

Additional features and descriptions of the poly(ester-amide) polymers (PEA) are provided, for example, in US Re40,359, which is a reissue of U.S. Pat. No. 6,703,040.

Hydrophobic Derivatives of Natural Biodegradable Polysaccharides

One suitable class of biodegradable polymers useful in the present invention includes the hydrophobic derivatives of natural biodegradable polysaccharides. Hydrophobic derivatives of natural biodegradable polysaccharide refer to a natural biodegradable polysaccharide having one or more hydrophobic pendent groups attached to the polysaccharide. In many cases the hydrophobic derivative includes a plurality of groups that include hydrocarbon segments attached to the polysaccharide. When a plurality of groups including hydrocarbon segments are attached, they are collectively referred to as the "hydrophobic portion" of the hydrophobic derivative. The hydrophobic derivatives therefore include a hydrophobic portion and a polysaccharide portion.

The polysaccharide portion includes a natural biodegradable polysaccharide, which refers to a non-synthetic polysaccharide that is capable of being enzymatically degraded. Natural biodegradable polysaccharides include polysaccharide and/or polysaccharide derivatives that are obtained from natural sources, such as plants or animals. Natural biodegradable polysaccharides include any polysaccharide that has been processed or modified from a natural biodegradable polysaccharide (for example, maltodextrin is a natural biodegradable polysaccharide that is processed from starch). Exemplary natural biodegradable polysaccharides include maltodextrin, amylose, cyclodextrin, polyalditol, hyaluronic acid, dextran, heparin, chondroitin sulfate, dermatan sulfate, heparan sulfate, keratan sulfate, dextran, dextran sulfate, pentosan polysulfate, and chitosan. Specific polysaccharides are low molecular weight polymers that have little or no branching, such as those that are derived from and/or found in starch preparations, for example, maltodextrin, amylose, and cyclodextrin. Therefore, the natural biodegradable polysaccharide can be a substantially non-branched or completely non-branched poly(glucopyranose) polymer.

"Amylose" or "amylose polymer" refers to a linear polymer having repeating glucopyranose units that are joined by α-1,4 linkages. Some amylose polymers can have a very small amount of branching via linkages (about less than 0.5% of the linkages) but still demonstrate the same physical properties as linear (unbranched) amylose polymers do. Generally amylose polymers derived from plant sources have molecular weights of about $1 \times 10^6$ Da or less. Amylopectin, comparatively, is a branched polymer having repeating glucopyranose units that are joined by α-1,4 linkages to form linear portions and the linear portions are linked together via α-1,6 linkages. The branch point linkages are generally greater than 1% of the total linkages and typically 4%-5% of the total linkages. Generally amylopectin derived from plant sources have molecular weights of $1 \times 10^7$ Da or greater.

For example, in some aspects, starch preparations having a high amylose content, purified amylose, synthetically prepared amylose, or enriched amylose preparations can be used in the preparation of a hydrophobic derivative of amylose. In some embodiments the composition includes a mixture of polysaccharides including amylose wherein the amylose content in the mixture of polysaccharides is 50% or greater, 60% or greater, 70% or greater, 80% or greater, or 85% or greater by weight. In other embodiments the composition includes a mixture of polysaccharides including amylose and amylopectin and wherein the amylopectin content in the mixture of polysaccharides is 30% or less, or 15% or less.

The amount of amylopectin present in a starch can be reduced by treating the starch with amylopectinase, which cleaves α-1,6 linkages resulting in the debranching of amylopectin into amylose. Steps may be performed before, during, and/or after the process of derivatizing the amylose polymer with a pendent group comprising a hydrocarbon segment to enrich the amount of amylose, or purify the amylose.

Amylose of particular molecular weights can be obtained commercially or can be prepared. For example, synthetic amyloses with average molecular masses of 70 kDa, 110 kDa, and 320 kDa, can be obtained from Nakano Vinegar Co., Ltd. (Aichi, Japan). Purified or enriched amylose preparations can be obtained commercially or can be prepared using standard biochemical techniques such as chromatography. In some aspects, high-amylose cornstarch can be used to prepare the hydrophobic derivative.

Maltodextrin is typically generated by hydrolyzing a starch slurry with heat-stable α-amylase at temperatures at 85-90° C. until the desired degree of hydrolysis is reached and then inactivating the α-amylase by a second heat treatment. The maltodextrin can be purified by filtration and then spray dried to a final product. Maltodextrins are typically characterized by their dextrose equivalent (DE) value, which is related to the degree of hydrolysis defined as: DE=MW dextrose/number-averaged MW starch hydrolysate X 100. Generally, maltodextrins are considered to have molecular weights that are less than amylose molecules. Maltodextrins of various molecular weights, for example, in the range of about 500 Da to 5000 Da are commercially available (for example, from CarboMer, San Diego, Calif.).

Another contemplated class of natural biodegradable polysaccharides is natural biodegradable non-reducing polysaccharides. A non-reducing polysaccharide refers to a polymer of non-reducing disaccharides (two monosaccharides linked through their anomeric centers) such as trehalose (α-D-glucopyranosyl α-D-glucopyranoside) and sucrose (β-D-fructofuranosyl α-D-glucopyranoside). An exemplary non-reducing polysaccharide includes polyalditol which is available from GPC (Muscatine, Iowa). In another aspect, the polysaccharide is a glucopyranosyl polymer, such as a polymer that includes repeating (1→3)O-β-D-glucopyranosyl units.

Dextran is an α-D-1,6-glucose-linked glucan with side-chains 1-3 linked to the backbone units of the dextran biopolymer. Dextran includes hydroxyl groups at the 2, 3, and 4 positions on the glucopyranose monomeric units. Dextran can be obtained from fermentation of sucrose-containing media by Leuconostoc mesenteroides B512F. Dextran can be obtained in low molecular weight preparations. Enzymes (dextranases) from molds such as Penicillium and Verticillium have been shown to degrade dextran. Similarly many bacteria produce extracellular dextranases that split dextran into low molecular weight sugars.

Chondroitin sulfate includes the repeating disaccharide units of D-galactosamine and D-glucuronic acid, and typically contains between 15 to 150 of these repeating units. Chondroitinase AC cleaves chondroitin sulfates A and C, and chondroitin.

Hyaluronic acid (HA) is a naturally derived linear polymer that includes alternating β-1,4-glucuronic acid and β-3-1,3-N-acetyl-D-glucosamine units. HA is the principal glycosaminoglycan in connective tissue fluids. HA can be fragmented in the presence of hyaluronidase.

In many aspects the polysaccharide portion and the hydrophobic portion include the predominant portion of the hydrophobic derivative of the natural biodegradable polysaccharide. Based on a weight percentage, the polysaccharide portion can be about 25% wt of the hydrophobic derivative or greater, in the range of about 25% to about 75%, in the range of about 30% to about 70%, in the range of about 35% to about 65%, in the range of about 40% to about 60%, or in the range of about 45% to about 55%. Likewise, based on a weight percentage of the overall hydrophobic derivative, the hydrophobic portion can be about 25% wt of the hydrophobic derivative or greater, in the range of about 25% to about 75%, in the range of about 30% to about 70%, in the range of about 35% to about 65%, in the range of about 40% to about 60%, or in the range of about 45% to about 55%. In exemplary aspects, the hydrophobic derivative has approximately 50% of its weight attributable to the polysaccharide portion, and approximately 50% of its weight attributable to its hydrophobic portion.

The hydrophobic derivative is insoluble in water. For example, the solubility can be less than or equal to 1 part solute per 10,000 parts or greater solvent.

A hydrophobic derivative can be prepared by associating one or more hydrophobic compound(s) with a natural biodegradable polysaccharide polymer. The hydrophobic derivatives of the natural biodegradable polysaccharides specifically have an average molecular weight of up to about 1,000,000 Da, up to about 300,000 Da or up to about 100,000 Da. In some aspects the hydrophobic derivatives have a molecular weight of about 250,000 Da or less, about 100,000 Da or less, about 50,000 Da or less, or 25,000 Da or less. Particularly specific size ranges for the natural biodegradable polysaccharides are in the range of about 2,000 Da to about 20,000 Da, or about 4,000 Da to about 10,000 Da.

The molecular weight of the polymer is more precisely defined as "weight average molecular weight" or $M_w$. $M_w$ is an absolute method of measuring molecular weight and is particularly useful for measuring the molecular weight of a polymer.

In some aspects, the addition of hydrophobic portion causes an increase in molecular weight of the polysaccharide of about 20% or greater, about 50% or greater, about 75% or greater, about 100% or greater, or about 125%, the increase in relation to the underivatized form of the polysaccharide. As an example, a maltodextrin having a starting weight of about 3000 Da can be derivatized to provide pendent hexanoate groups that are coupled to the polysaccharide via ester linkages to provide a degree of substitution (DS) of about 2.5. This provides a hydrophobic polysaccharide having a theoretical molecular weight of about 8400 Da.

In forming the hydrophobic derivative of the natural biodegradable polysaccharide and as an example, a compound having a hydrocarbon segment can be covalently coupled to one or more portions of the polysaccharide. For example, the compound can be coupled to monomeric units along the length of the polysaccharide. This provides a polysaccharide derivative with one or more pendent groups. Each chemical group includes a hydrocarbon segment. The hydrocarbon segment can constitute all of the pendent chemical group, or the hydrocarbon segment can constitute a portion of the pendent chemical group. For example, a portion of the hydrophobic polysaccharide can have the following structural formula (I):

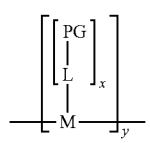

(I)

wherein each M is independently a monosaccharide unit, each L is independently a suitable linking group, or is a direct bond, each PG is independently a pendent group, each x is independently 0 to about 3, such that when x is 0, the bond between L and M is absent, and y is 3 or more.

Additionally, the polysaccharide that includes the unit of formula (I) above can be a compound of formula (II):

(II)

wherein each M is independently a monosaccharide unit, each L is independently a suitable linking group, or is a direct bond, each PG is independently a pendent group, each x is independently 0 to about 3, such that when x is 0, the bond between L and M is absent, y is about 3 to about 5,000, and $Z^1$ and $Z^2$ are each independently hydrogen, $OR^1$, $OC(=O)R^1$, $CH_2OR^1$, $SiR^1$ or $CH_2OC(=O)R^1$. Each $R^1$ is independently hydrogen, alkyl, cycloalkyl, cycloalkyl alkyl, aryl, aryl alkyl, heterocyclyl or heteroaryl, each alkyl, cycloalkyl, aryl, heterocycle and heteroaryl is optionally substituted, and each alkyl, cycloalkyl and heterocycle is optionally partially unsaturated.

For the compounds of formula (I) and (II), the monosaccharide unit (M) can include D-glucopyranose (e.g., α-D-glucopyranose). Additionally, the monosaccharide unit (M) can include non-macrocyclic poly-α(1→4) glucopyranose, non-macrocyclic poly-α(1→6) glucopyranose, or a mixture or combination of both non-macrocyclic poly-α(1→4) glucopyranose and non-macrocyclic poly-α(1→6) glucopyranose. For example, the monosaccharide unit (M) can include glucopyranose units, wherein at least about 90% are linked by α(1→4)glycosidic bonds. Alternatively, the monosaccharide unit (M) can include glucopyranose units, wherein at least about 90% are linked by α(1→6)glycosidic bonds. Additionally, each of the monosaccharides in the polysaccharide can be the same type (homopolysaccharide), or the monosaccharides in the polysaccharide can differ (heteropolysaccharide).

The polysaccharide can include up to about 5,000 monosaccharide units (i.e., y in the formula (I) or (II) is up to 5,000). Specifically, the monosaccharide units can be glucopyranose units (e.g., α-D-glucopyranose units). Additionally, y in the formula (I) or (II) can specifically be about 3-5,000 or about 3-4,000 or about 100 to 4,000.

In specific embodiments, the polysaccharide is non-macrocyclic. In other specific embodiments, the polysaccharide is linear. In other specific embodiments, the polysaccharide is branched. In yet further specific embodiments, the polysaccharide is a natural polysaccharide (PS).

The polysaccharide will have a suitable glass transition temperature (Tg). In an embodiment, the polysaccharide will have a glass transition temperature (Tg) of at least about 35° C. (e.g., about 40° C. to about 150° C.). In an embodiment, the polysaccharide will have a glass transition temperature (Tg) of −30° C. to about 0° C.

A hydrocarbon segment can include saturated hydrocarbon groups or unsaturated hydrocarbon groups, and examples thereof include alkyl, alkenyl, alkynyl, cyclic alkyl, cyclic alkenyl, aromatic hydrocarbon and aralkyl groups. Specifically, the pendant group includes linear, straight chain or branched $C_1$-$C_{20}$ alkyl group; an amine terminated hydrocarbon or a hydroxyl terminated hydrocarbon. In an embodiment, the pendant group includes poly-esters such as polylactides, polyglycolides, poly(lactide-co-glycolide) co-polymers, polycaprolactone, terpolymers of poly(lactide-co-glycolide-co-caprolatone), or combinations thereof.

Chemical linkages (e.g., metabolically cleavable covalent bonds) that can be used to bond the pendent groups to the polysaccharide include carboxylic ester, carbonate, borate, silyl ether, peroxyester groups, disulfide groups, and hydrazone groups. In some cases, the hydroxyl reactive groups include those such as isocyanate and epoxy. These groups can be used to form a non-cleavable covalent bond between the pendent group and the polysaccharide backbone. In these aspects, the synthesized hydrophobic derivative of the natural biodegradable polysaccharide includes chemical linkages that are enzymatically cleavable.

Other reactive groups, such as carboxyl groups, acetyl groups, or sulphate groups, are present on the ring structure of monomeric units of other natural biodegradable polysaccharides, such as chondrotin or hyaluronic acid. These groups can also be targeted for reaction with a compound having a hydrocarbon segment to be bonded to the polysaccharide backbone.

The weight ratio of glucopyranose units to pendent groups can vary, but will typically be about 1:1 to about 100:1. Specifically, the weight ratio of glucopyranose units to pendent groups can be about 1:1 to about 75:1, or about 1:1 to about 50:1. Additionally, the nature and amount of the pendent group can provide a suitable degree of substitution to the polysaccharide. Typically, the degree of substitution will be in the range of about 0.1-5 or about 0.5-2.

The degree of substitution can influence the hydrophobic character of the polysaccharide. In turn, implants formed from hydrophobic derivatives having a substantial amount of groups having the hydrocarbon segments bonded to the polysaccharide backbone (as exemplified by a high DS) are generally more hydrophobic and can be more resistant to degradation. For example, an implant formed from maltodextrin-butyrate DS1 has a rate of degradation that is faster than an implant formed from maltodextrin-butyrate DS2.

The type of hydrocarbon segment present in the groups pendent from the polysaccharide backbone can also influence the hydrophobic properties of the polymer. In one aspect, the implant is formed using a hydrophobic polysaccharide having pendent groups with hydrocarbon segments being short chain branched alkyl group. Exemplary short chain branched alkyl group are branched $C_4$-$C_{10}$ groups. The preparation of a hydrophobic polymer with these types of pendent groups is exemplified by the reaction of maltodextrin with valproic acid/anhydride with maltodextrin (MD-val). The reaction can be carried out to provide a relatively lower degree of substitution of the hydroxyl groups, such as is in the range of 0.5-1.5. Although these polysaccharides have a lower degree of substitution, the short chain branched alkyl group imparts considerable hydrophobic properties to the polysaccharide.

In some aspects, the pendent group includes a hydrocarbon segment that is a linear, branched, or cyclic $C_2$-$C_{18}$ group. More specifically the hydrocarbon segment includes a $C_2$-$C_{10}$, or a $C_4$-$C_8$, linear, branched, or cyclic group. The hydrocarbon segment can be saturated or unsaturated, and can include alkyl groups or aromatic groups, respectively. The hydrocarbon segment can be linked to the polysaccharide chain via a hydrolyzable bond or a non-hydrolyzable bond.

In some aspects the compound having a hydrocarbon segment that is reacted with the polysaccharide backbone is derived from a natural compound. Natural compounds with hydrocarbon segments include fatty acids, fats, oils, waxes, phospholipids, prostaglandins, thromboxanes, leukotrienes, terpenes, steroids, and lipid soluble vitamins.

Exemplary natural compounds with hydrocarbon segments include fatty acids and derivatives thereof, such as fatty acid anhydrides and fatty acid halides. Exemplary fatty acids and anhydrides include acetic, propionic, butyric, isobutyric, valeric, caproic, caprylic, capric, and lauric acids and anhydrides, respectively. The hydroxyl group of a polysaccharide can be reacted with a fatty acid or anhydride to bond the hydrocarbon segment of the compound to the polysaccharide via an ester group.

The hydroxyl group of a polysaccharide can also cause the ring opening of lactones to provide pendent open-chain hydroxy esters. Exemplary lactones that can be reacted with the polysaccharide include caprolactone and glycolides.

Additional features and descriptions of the biodegradable polymers that include the hydrophobic derivatives of natural biodegradable polysaccharides can be found, for example, in U.S. Patent Publication Nos. 2007/0218102, 2007/0260054 and 2007/0224247, and references cited therein.

Balloon Catheters

In an embodiment, the insertable medical device can be used for the treatment of diseased vasculature. Suitable bioactive agents that can be released to the vasculature include an antiproliferative agent, an antiinflammatory agent, an antiplatelet agent, or plurality thereof. Suitable antiproliferative agents include paclitaxel. Balloon catheters are commonly used in angioplasty procedures for the treatment of arteries that are diseased. Balloon angioplasty generally involves the dilation or reopening of blocked intraluminal channels.

Balloon catheter constructions are well known in the art and are described in various documents, for example, U.S. Pat. Nos. 4,195,637, 5,041,089, 5,087,246, 5,318,587, 5,382,234, 5,571,089, 5,776,101, 5,807,331, 5,882,336, 6,394,995, 6,517,515, 6,623,504, 6,896,842, and 7,163,523. Balloon catheters generally include four portions, the balloon, catheter shaft, guidewire, and manifold. A balloon catheter generally includes an elongated catheter shaft with the inflatable balloon attached to a distal section of the catheter shaft. At a proximal end of the catheter shaft, there is typically a manifold. At the manifold end, placement of the catheter can be facilitated using a guidewire. Guidewires are small and maneuverable when inserted into an artery. Once the guidewire is moved to the target location, the catheter with balloon portion is then fed over the guidewire until the balloon reaches the target location in the vessel. The balloon is then inflated when the catheter reaches the targeted constriction to thereby apply the requisite mechanical force to cause vessel dilation. The manifold can also control the fluid introduction within shaft for expansion of the balloon. The balloon is typically inserted into the arterial lumen of a patient and advanced through the lumen in an unexpanded state.

Prior to inflation the balloon can be folded to a compacted configuration for delivery to the target site. A folding process may involve creating "arms" of the balloon material and folding these arms inward (towards the catheter axis) to compact the balloon material. Using such a folding pattern, there will be portions of the balloon material (when the balloon is folded and compacted) that face the outside, and portions of the balloon material that face the inside, the inner-facing portions representing "protected" surfaces.

Accordingly, and in another coating embodiment, the inner-facing surfaces of the balloon material include the present coating.

The balloon is typically inflated using a fluid, which is injected through an inflation port. The mechanics of fluid transfer and introduction within balloons vary according to the specific design of the catheter, and are well know in the art.

Exemplary thicknesses for the walls of catheter balloons are in the range of about 5 µm to about 20 µm. The actual thickness of the balloon wall may depend on one or more factors, such as the desired pliability of the balloon, the overall profile of the balloon on the catheter (low profile devices may use thin walled balloons), the pressure rating for the balloon wall, or the expansion properties of the balloon. In some cases, a balloon with a thin wall is used, so as to accommodate the increase in thickness when a coating is formed on the surface.

Catheter balloon construction is described in various references, for example, U.S. Pat. Nos. 4,490,421, 5,556,383, 6,210,364, 6,168,748, 6,328,710, and 6,482,348. Molding processes are typically performed for balloon construction. Balloons fabricated by such processes are suitable as substrates for the coatings according to the present invention. In an exemplary molding process, an extruded polymeric tube is radially and axially expanded at elevated temperatures within a mold having the desired shape of the balloon. The balloon can be subjected to additional treatments following the molding process. For example, the formed balloon can be subjected to additional heating steps to reduce shrinkage of the balloon.

The present invention may be better understood with reference to the following examples. These examples are intended to be representative of specific embodiments of the invention, and are not intended as limiting the scope of the invention.

EXAMPLE

The Present Pharmaceutical Composition Increased Paclitaxel Penetration into and Through Arterial Tissue Certain embodiments of the present pharmaceutical composition increased transfer of paclitaxel from a balloon catheter into and through arterial tissue in an ex-vivo model.

Preparing a Double Wall Catheter Containing the Present Therapeutic Composition

Holes were poked in thin walled silicone tubing with a piece of 0.014 inch diameter nitinol wire. The tubing was then washed extensively and repeatedly—a sonication, washing with hot water and an alkaline detergent, followed by two more sonications. The tubing was then coated with first coat of a scissile coating. It was immersed in a 2 mg/ml solution of photo-polyvinylpyrrolidone (as described in U.S. Pat. No. 6,007,833) in deionized water, bubbles were removed, and it was subjected to UV cure (Dymax 2000-EC Series UV Floodlamp with a 400 Watt metal halide bulb, approximately 20 cm from light source, illuminated for four minutes). Then the tubing was slowly removed from the solution with a tweezers, drained, fluid was wicked from the interior. The tubing was allowed to dry for about 5 min with a gentle flow of nitrogen through the inside of the tubes.

The tubing was then immersed for a second coat of scissile coating. The second coat was also photo-polyvinylpyrrolidone (as described in U.S. Pat. No. 6,007,833), but in isopropanol. The tubing was then removed from the coating solution, drained, wicked, dried, and uv cured for three minutes.

The tubing was then immersed for a third coat of scissile coating. The third coat was also photo-polyacrylamide (as described in U.S. Pat. No. 6,007,833) in a solvent of 43% deionized water and 57% isopropanol. After 30 seconds in the coating composition, the tubing was removed, drained, quickly wicked, and uv cured for three minutes. The tubing was then dried and uv cured again for 3 minutes.

A balloon catheter was obtained from Minnesota Medtec (Maple Grove, Minn.); the balloon was made from nylon with a wall thickness of 5-10 µm. The silicone tubing with the scissile coating was placed over the first balloon of the catheter and one end was fixed in place. The reservoir was filled by injecting the present therapeutic composition including glycofurol and paclitaxel. The second end was then fixed to seal the reservoir.

The catheter was pressurized at 4 to 8 atm to inflate, and therapeutic composition was expelled from the device.

Ex Vivo Testing

Harvested porcine artery was obtained and cut into 1.5 inch lengths. The porcine artery pieces were then placed in a 4 mL amber glass vial filled with 4 mL of PBS (phosphate buffered saline) at pH 7.4, which was preheated in a water bath to 37° C.

In one test, the double wall balloon was soaked in buffer before being applied to the porcine artery. The double balloon assembly was placed in an 8 mL vial that had been filled with 8 mL of PBS at pH 7.4 and preheated in a water bath to 37° C. and soaked for 4 min.

In both tests, the balloon was slid into the inner lumen of the porcine artery (submerged inside 4 mL vial) and then expanded for 30 sec at 4 atm. Pressure was then released and the balloon was removed from the porcine artery. To determine the amount of paclitaxel transferred to the wall of the inner lumen of the porcine artery, the porcine artery was extracted with methanol and the methanol was subjected to HPLC to detect the paclitaxel.

Results and Conclusion

In a first test, a balloon was coated with a composition of 30 wt-% taxol and 70 wt-% glycofurol. A total of 5432 µg paclitaxel was deposited on the balloon and 40% of it was delivered to the arterial tissue. The paclitaxel penetrated the artery and crystals of paclitaxel formed on the outside of the piece of artery. The present composition resulted in delivery of paclitaxel to the tissue and uptake into and through the tissue. In this test, the balloon was soaked in buffer before being applied to the artery.

In a second test, a balloon was coated with a composition of 10 wt-% taxol and 90 wt-% glycofurol. A total of 566 µg paclitaxel was deposited on the balloon and 37% of it was delivered to the arterial tissue. The paclitaxel was apparently absorbed by the tissue, as none was observed on the surface of the tissue.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

It should also be noted that, as used in this specification and the appended claims, the term "configured" describes a system, apparatus, or other structure that is constructed or configured to perform a particular task or adopt a particular configuration. The term "configured" can be used interchangeably with other similar phrases such as arranged and configured, constructed and arranged, adapted and configured, adapted, constructed, manufactured and arranged, and the like.

All publications and patent applications in this specification are indicative of the level of ordinary skill in the art to which this invention pertains.

The invention has been described with reference to various specific and preferred embodiments and techniques. However, it should be understood that many variations and modifications may be made while remaining within the spirit and scope of the invention.

I claim:

1. An intra-arterial catheter comprising a reservoir consisting of a pharmaceutical composition solution of paclitaxel in an amount in the range of 5 to 40 wt-% and glycofurol in an amount in the range of 60 to 95 wt-% wherein paclitaxel and glycofurol total 100% of components of the pharmaceutical composition solution, wherein the reservoir delivers the pharmaceutical composition solution to an exposed interior surface of an artery using a balloon in order for the paclitaxel to appear as a solid on the exterior of the artery after delivery to the interior surface of the artery to treat arterial disease, said arterial disease characterized by blocked intraluminal channel(s), wherein (a) the balloon of the catheter comprises an inner expandable and collapsible structure and an outer expandable and collapsible structure, the inner and outer expandable and collapsible structures configured to expand between a contracted state and a dilated state, the inner and outer expandable and collapsible structures defining a cavity therebetween which is the reservoir for the composition, wherein the outer expandable and collapsible structure comprises openings in the dilated state that allow the composition solution to move from the reservoir to the interior surface of an artery, or (b) the catheter comprises a catheter shaft, and the reservoir is a lumen in the catheter shaft and in fluid communication with the balloon, and the composition solution is released from the balloon upon expansion of the balloon.

2. The catheter of claim 1, wherein the pharmaceutical composition solution has paclitaxel in an amount in the range of about 5 to about 10 wt-% and glycofurol in an amount in the range of about 90 to about 95 wt-%.

3. The catheter of claim 1, wherein the pharmaceutical composition solution has paclitaxel in an amount in the range of about 10 to about 30 wt-% and glycofurol in an amount in the range of about 70 to about 90 wt-%.

4. The catheter of claim 1, wherein the pharmaceutical composition solution has paclitaxel in an amount in the range of about 5 to about 15 wt-% and glycofurol in an amount in the range of about 85 to about 95 wt-%.

5. The catheter of claim 1, wherein the pharmaceutical composition solution has paclitaxel in an amount in the range of about 10 to about 20 wt-% and glycofurol in an amount in the range of about 85 to about 95 wt-%.

6. The catheter of claim 1, wherein the pharmaceutical composition solution has paclitaxel in an amount in the range of about 20 to about 30 wt-% and glycofurol in an amount in the range of about 70 to about 80 wt-%.

7. The catheter of claim 1 comprising a polymer coating on the outer surface of the outer expandable and collapsible structure.

8. The catheter of claim 1, wherein the paclitaxel functions as an antiproliferative agent for the treatment of diseased arterial tissue that causes the blocked intraluminal channel(s).

9. The catheter of claim 1, wherein the interior surface of the artery having said arterial disease is also treated by expansion of the balloon of the balloon catheter.

10. The catheter of claim 1, wherein the openings in the outer expandable and collapsible structure are configured to be closed when the structure is in the contracted state.

* * * * *